US00PP21939P2

(12) United States Plant Patent
Misato

(10) Patent No.: US PP21,939 P2
(45) Date of Patent: May 31, 2011

(54) ***MANDEVILLA* PLANT NAMED 'SUNPARAROPI'**

(50) Latin Name: *Mandevilla hybrida*
Varietal Denomination: Sunpararopi

(75) Inventor: Tomoya Misato, Yamanashi (JP)

(73) Assignee: Suntory Flowers Ltd., Tokyo (JP)

( * ) Notice: Subject to any disclaimer, the term of this patent is extended or adjusted under 35 U.S.C. 154(b) by 0 days.

(21) Appl. No.: 12/658,731

(22) Filed: Feb. 12, 2010

(51) Int. Cl.
*A01H 5/00* (2006.01)

(52) U.S. Cl. ..... Plt./232

(58) Field of Classification Search ..... Plt./232
See application file for complete search history.

*Primary Examiner* — Kent L Bell
(74) *Attorney, Agent, or Firm* — C. A. Whealy

(57) ABSTRACT

A new and distinct cultivar of *Mandevilla* plant named 'Sunpararopi', characterized by its vining plant habit; vigorous growth habit; relatively small glossy leaves; freely branching and flowering habit; medium-sized reddish pink-colored flowers; and long flowering period.

1 Drawing Sheet

Botanical designation: *Mandevilla hybrida.*
Cultivar denomination: 'SUNPARAROPI'.

BACKGROUND OF THE INVENTION

The present invention relates to a new and distinct cultivar of *Mandevilla* plant, botanically known as *Mandevilla hybrida* and hereinafter referred to by the name 'Sunpararopi'.

The new *Mandevilla* plant is a product of a planned breeding program conducted by the Inventor in Higashiomi, Shiga, Japan. The objective of the breeding program is to create new vining and freely-branching *Mandevilla* plants with numerous small dark green-colored leaves and attractive flowers.

The new *Mandevilla* plant originated from a cross-pollination made by the Inventor in Higashiomi, Shiga, Japan in April, 2004, of a proprietary selection of *Mandevilla hybrida* identified as code number M35-4, not patented, as the female, or seed parent with a proprietary selection of *Mandevilla hybrida* identified as code number M28-3, not patented, as the male, or pollen, parent. The new *Mandevilla* plant was discovered and selected by the Inventor as a single flowering plant from within the progeny of the stated cross-pollination in a controlled greenhouse environment in Higashiomi, Shiga, Japan in November, 2005.

Asexual reproduction of the new *Mandevilla* plant by cuttings in Higashiomi, Shiga, Japan, since December, 2005, has shown that the unique features of this new *Mandevilla* plant are stable and reproduced true to type in successive generations.

SUMMARY OF THE INVENTION

Plants of the new *Mandevilla* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Sunpararopi'. These characteristics in combination distinguish 'Sunpararopi' as a new and distinct cultivar:

1. Vining plant habit.
2. Vigorous growth habit.
3. Relatively small glossy leaves.
4. Freely branching and flowering habit.
5. Medium-sized reddish pink-colored flowers.
6. Long flowering period.

Plants of the new *Mandevilla* can be compared to plants of the female parent selection. Plants of the new *Mandevilla* differ primarily from plants of the female parent selection in the following characteristics:

1. Plants of the new *Mandevilla* are more vigorous than plants of the female parent selection.
2. Plants of the new *Mandevilla* and the female parent selection differ in flower color as plants of the female parent selection have red-colored flowers.

Plants of the new *Mandevilla* can be compared to plants of the male parent selection. Plants of the new *Mandevilla* differ primarily from plants of the male parent selection in flower color as plants of the male parent selection have pale pink-colored flowers.

Plants of the new *Mandevilla* can be compared to plants of the *Mandevilla* 'Sunmandecripi', disclosed in a U.S. Plant Pat. No. 18,578. In side-by-side comparisons conducted in Higashiomi, Shiga, Japan, plants of the new *Mandevilla* differed from plants of 'Sunmandecripi' in the following characteristics:

1. Plants of the new *Mandevilla* were more vigorous than plants of 'Sunmandecripi'.
2. Plants of the new *Mandevilla* were shorter than plants of 'Sunmandecripi'.
3. Plants of the new *Mandevilla* had thicker stems than plants of 'Sunmandecripi'.
4. Plants of the new *Mandevilla* had smaller leaves than plants of 'Sunmandecripi'.
5. Plants of the new *Mandevilla* had smaller flowers than plants of 'Sunmandecripi'.
6. Plants of the new *Mandevilla* and 'Sunmandecripi' differed in flower color as plants of '. Sunmandecripi' had red purple-colored flowers.

BRIEF DESCRIPTION OF THE PHOTOGRAPHS

The accompanying colored photographs illustrate the overall appearance of the new *Mandevilla* plant, showing the colors as true as it is reasonably possible to obtain in colored reproductions of this type. Colors in the photographs may differ slightly from the color values cited in the detailed botanical description which accurately describe the actual colors of the new *Mandevilla* plant.

The photograph at the top of the sheet comprises a side perspective view of a typical flowering plant of 'Sunpararopi' grown in a container.

The photograph at the bottom of the sheet is a close-up view of a typical flowering plant of 'Sunpararopi'.

DETAILED BOTANICAL DESCRIPTION

The aforementioned photographs and following observations, measurements and values describe plants grown in 15-cm containers in Higashiomi, Shiga, Japan, under commercial practice during the summer in an outdoor nursery. During the production of the plants, day temperatures averaged 25° C. and night temperatures averaged 15° C. Plants were five and six months old when the description and photographs, respectively, were taken. In the following description, color references are made to The Royal Horticultural Society Colour Chart, 2001 Edition, except where general terms of ordinary dictionary significance are used.

Botanical classification: *Mandevilla hybrida* 'Sunpararopi'.

Parentage:

*Female, or seed, parent.*—Proprietary selection of *Mandevilla hybrida* identified as code number M35-4, not patented.

*Male, or pollen, parent.*—Proprietary selection of *Mandevilla hybrida* identified as code number M28-3, not patented.

Propagation:

*Type.*—By vegetative cuttings.

*Time to initiate roots.*—About two weeks at 23° C. to 25° C.

*Time to produce a rooted young plant.*—About five to six weeks at 23° C. to 25° C.

*Root description.*—Fibrous; light brown in color.

*Rooting habit.*—Freely branching; moderately dense.

Plant description:

*Plant and growth habit.*—Vining plant habit; vigorous growth habit; freely branching habit.

*Plant height.*—About 45 cm to 200 cm.

*Lateral branch description.*—Diameter: About 3.5 mm. Internode length: About 1.5 cm to 15 cm. Strength: Strong. Texture: Smooth, glabrous. Color, young: Close to 144A. Color, mature: Close to 199A.

Foliage description:

*Arrangement.*—Opposite, simple.

*Length.*—About 6 cm.

*Width.*—About 3.4 cm.

*Shape.*—Elliptic.

*Apex.*—Cuspidate.

*Base.*—Obtuse.

*Margin.*—Entire.

*Texture, upper and lower surfaces.*—Smooth, glabrous.

*Luster, upper and lower surfaces.*—Glossy.

*Venation pattern.*—Pinnate, reticulate.

*Color.*—Developing leaves, upper surface: Close to 137B. Developing leaves, lower surface: Close to 138B. Fully expanded leaves, upper surface: Close to 137A; venation, close to 145B. Fully expanded leaves, lower surface: Close to 138B; venation, close to 145B.

*Petiole length.*—About 1.7 cm.

*Petiole diameter.*—About 1.3 mm.

*Petiole texture, upper and lower surfaces.*—Smooth, glabrous.

*Petiole color, upper and lower surfaces.*—Close to 146D tinted with close to 176B.

Flower description:

*Flower type and habit.*—Single salverform flowers; flowers arranged in racemes; flowers face mostly outwardly; freely flowering habit with about two to five flowers per inflorescence.

*Natural flowering season.*—Plants begin flowering about six weeks after planting; long flowering period; plants flower continuously from early summer to late autumn in Japan.

*Flower longevity on the plant.*—About seven to ten days; flowers not persistent.

*Fragrance.*—Faint, pleasant.

*Inflorescence height.*—About 12 cm.

*Inflorescence diameter.*—About 10 cm.

*Flowers.*—Appearance: Flared trumpet, corolla fused and five-parted; flowers roughly star-shaped. Diameter: About 7 cm. Depth (length): About 6.8 cm. Throat diameter: About 1.54 cm. Tube length: About 6 cm. Tube diameter, mid-section: About 1.44 cm. Tube diameter, base: About 3.4 mm.

*Flower buds.*—Height: About 7.6 cm. Diameter: About 1.3 cm. Shape: Lenticular. Color: Close to 58A.

*Corolla.*—Arrangement/appearance: Single whorl of five petals, fused at the base. Petal length: About 2.8 cm. Petal width: About 2.1 cm. Petal shape: Spatulate. Petal apex: Acuminate. Petal margin: Entire; slightly undulate. Petal texture, upper and lower surfaces: Smooth, glabrous. Throat texture: Smooth, glabrous. Tube texture: Smooth, glabrous. Color: Petal, when opening and fully opened, upper surface: Close to 53C; color becoming close to 155D tinted with close to 53C. Petal, when opening and fully opened, lower surface: Close to 60D. Tube: Close to 63C; towards the apex, close to N34A; towards the base, close to 150D. Throat: Close to 17C.

*Corona.*—Arrangement/appearance: Single whorl of five sepals, fused at the base. Sepal length: About 8.8 mm. Sepal width: About 2.1 mm. Sepal shape: Lanceolate. Sepal apex: Acute. Sepal base: Truncate. Sepal margin: Entire. Sepal texture, upper and lower surfaces: Smooth, glabrous. Sepal color: Immature, upper and lower surfaces: Close to 152D with reddish tinge. Mature, upper and lower surfaces: Close to 152D with reddish tinge.

*Peduncles.*—Length: About 6.5 cm. Diameter: About 1.4 mm. Texture: Smooth, glabrous. Strength: Flexible, but strong. Color: Close to 144A.

*Pedicels.*—Length: About 1.6 cm. Diameter: About 2 mm. Texture: Smooth, glabrous. Strength: Flexible, but strong. Color: Close to 199A.

*Reproductive organs.*—Stamens: Quantity/arrangement: Typically five; filaments fused to corolla; anthers, connivent. Anther shape: Ellipsoidal. Anther size: About 9.5 mm by 1.5 mm. Anther color: Close to 11B. Pollen amount: Scarce. Pollen color: Close to 11B. Pistils: Quantity: Typically one. Pistil length: About 3.1 cm. Stigma shape: Conical. Stigma color: Close to 144B. Style color: Close to 145D. Ovary color: Close to 144A.

*Seed/fruit.*—Seed and fruit production have not been observed.

Disease/pest resistance: Plants of the new *Mandevilla* have not been noted to be resistant to pathogens and pests common to *Mandevilla* plants.

Garden performance: Plants of the new *Mandevilla* have been observed to tolerate wind, rain and temperatures ranging from about 4° C. to about 30° C.

It is claimed:

1. A new and distinct *Mandevilla* plant named 'Sunpararopi' as illustrated and described.

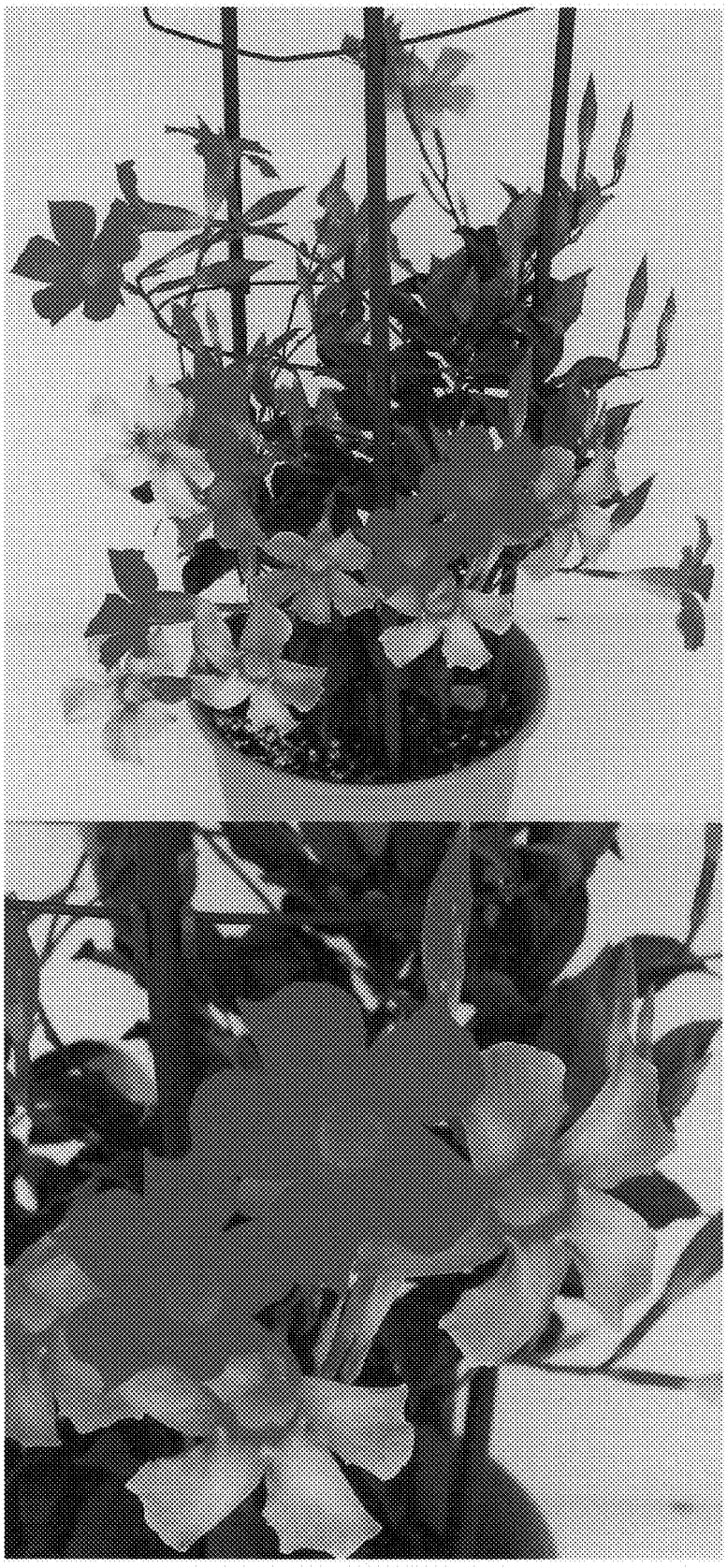

* * * * *